United States Patent
Hinnekens et al.

(12)

(10) Patent No.: US 6,224,783 B1
(45) Date of Patent: *May 1, 2001

(54) LUBRICATING COMPOUND FOR REFRIGERATION COMPRESSORS

(75) Inventors: Herve Hinnekens, Wetteren; Andre Demoulin, Beauvechanin, both of (BE)

(73) Assignee: Fina Research, S.A., Feluy (BE)

( * ) Notice: Subject to any disclaimer, the term of this patent is extended or adjusted under 35 U.S.C. 154(b) by 0 days.

This patent is subject to a terminal disclaimer.

(21) Appl. No.: 08/277,692

(22) Filed: Jul. 19, 1994

(30) Foreign Application Priority Data

Jul. 20, 1993 (EP) .................................................. 93870148

(51) Int. Cl.$^7$ ................... C10M 171/00; C10M 107/34; C07C 69/34; C09K 5/04
(52) U.S. Cl. ............................. 252/68; 508/455; 62/468; 554/227; 554/121; 560/198; 560/199
(58) Field of Search ..................................... 252/68, 52 A, 252/52 R; 508/455; 62/468; 554/227, 121; 560/198, 199

(56) References Cited

U.S. PATENT DOCUMENTS 3,871,837   3/1975   Bedague et al. .

5,250,205 * 10/1993 Akimoto et al. ...................... 508/466
5,370,809 * 12/1994 Ishida et al. ......................... 508/304

FOREIGN PATENT DOCUMENTS

| 0458584 | 5/1990 | (EP) . |
| 0461262 | 11/1990 | (EP) . |
| 461262 * | 12/1991 | (EP) . |
| 635562 * | 1/1995 | (EP) . |
| 187077 * | 1/1993 | (JP) . |
| 90/05172 | 5/1990 | (WO) . |
| 93/01249 | 1/1993 | (WO) . |

* cited by examiner

Primary Examiner—Alan Diamond
(74) Attorney, Agent, or Firm—Jim D. Wheelington

(57) ABSTRACT

The present invention provides a lubricating oil or a lubricating oil additive, particularly suitable for a R-134a (1,1,1,2-tetrafluoroethane) or R-134 (1,1,2,2-tetrafluoroethane) refrigerant, consisting of a compound (X) that can be prepared by esterification of a polyoxyethoxylated glycerol with at least one polycarboxylic acid compound having from 2 to 20 carbon atoms, preferably from 4 to 13 carbon atoms, and at least one monocarboxylic acid compound having from 2 to 20 carbon atoms, preferably from 6 to 13 carbon atoms.

6 Claims, No Drawings

LUBRICATING COMPOUND FOR REFRIGERATION COMPRESSORS

The present invention relates to a lubricating oil for compression type refrigerator systems. More particularly, it relates to a lubricating oil for compression type refrigerator systems having low hygroscopic properties, high thermal stability, high lubricating properties as well as good miscibility with refrigerants such as hydrofluorocarbons (HFC) including 1,1,1,2-tetrafluoroethane (hereinafter referred to as R-134a).

BACKGROUND OF THE INVENTION

Generally, a compression type refrigerator system is composed of a compressor, a condenser, an expansion valve and an evaporator, having a mechanism whereby a mixture of a refrigerant and a lubricating oil is circulating in the closed system. In said compression type refrigerator system, the temperature in the compressor generally rises to 50° C., while the temperature can also come to be of –40° C. or so, though it depends on the kind of apparatus. Accordingly, the refrigerant and the lubricating oil must circulate in this system without phase separation in the usual range of –40 to +50° C. If a phase separation occurs while the refrigerator system is running, it seriously affects the life and efficiency of the apparatus. For example, if phase separation of the refrigerant and the lubricating oil occurs in the compressor, the moving parts would be inadequately lubricated, resulting in seizure or other troubles, and thereby the life of apparatus would be shortened considerably. If phase separation occurs in the evaporator, the viscosity of the lubricating oil increases and thereby the efficiency of heat exchange is decreased.

Since a lubricating oil for refrigerator systems is used for the purpose of lubricating the moving parts of the refrigerator system, its lubricating properties are also important as a matter of course. Since the temperature becomes very high, particularly in the compressor, the oil is required to have a sufficient viscosity to retain the oil film necessary for lubricating.

The necessary viscosity varies with the kind of operating conditions of the compressor, but usually, the kinematic viscosity of the lubricating oil before mixing with a refrigerant is preferably 2 to 50 cSt at 100° C. If the kinematic viscosity is lower than the above, the oil film becomes thinner and thereby seizure is liable to arise, while if it is higher, the efficiency of heat exchange is decreased.

Heretofore, chlorofluorocarbons (CFC) including dichlorodifluoromethane (hereinafter referred to as R-12) has often been used as the refrigerant for compression type refrigerator systems, and various mineral oils and synthetic oils have been used as the lubricating oil, satisfying the required properties described above. R-12, however, has recently been restricted more and more severely all over the world, for the concern of environmental pollution problems, that is depletion of the ozone layer. Therefore, hydrofluorocarbons including R-134a have come to be noticed as possible refrigerant. Said hydrofluorocarbons, particularly R-134a have little possibility of depleting the ozone layer and can substitute for R-12, with minimal changes in the structure of the conventional refrigerator systems. Accordingly, it is presently preferred as a refrigerant for compression type refrigerator systems.

When hydrofluorocarbons including the above R-134a are employed as the refrigerant for compression type refrigerator systems instead of R-12, the desirable lubricating oils come to be those having high miscibility with said hydrofluorocarbons including R-134a, and also having high lubricating properties to satisfy the required properties described above. However, since the conventional lubricating oils which have been used with R-12 do not have good miscibility with hydrofluorocarbons including R-134a, a new lubricating oil suitable for said compounds is required. Further, particularly in air conditioners for automobiles, it is required that the equipment should preferably not be modified on the substitution for R-12.

Therefore it is not desirable to have to modify the present equipment because of phase separation due to lack of compatibility of the usual lubricating oils with HFC. Accordingly, a lubricating oil having very favorable miscibility with hydrofluorocarbons including R-134a is required.

As lubricating oils having miscibility with R-134a, polyalkyleneglycol compounds are known in the art, such as e.g. Ulcon LB-165 and Ulcon LB-525 (Ulcon is a tradename of Union Carbide Co., Ltd.).

Also, oil compositions for refrigerator systems with a high viscosity employing polyoxypropyleneglycol monobutyl ether as a base oil have been known (Japanese Patent Publication No. 42119/1982).

However it is known that such lubricating oils, which are polyalkyleneglycol derivatives having polypropyleneglycol with hydroxyl group at one terminal and an n-butyl ether bond at the other terminal, do not have sufficient miscibility with R-134a, and for example, Ulcon LB-525 described above is known to cause phase separation with R-134a at room temperature (U.S. Pat. No. 4,755,316).

On the other hand, polyoxyalkylene glycol having at least two hydroxyl groups in a molecule is proposed to be a favorable substance miscible with R-134a (U.S. Pat. No. 4,755,316). However the resulting refrigerant-lubricating oil compositions based on these compounds do not have the required properties.

U.S. Pat. No. 4,428,854 claims an absorption refrigerant composition comprising R-134a and at least one organic solvent selected from the group consisting of tetraethylene glycol dimethyl ether, dimethylformamide, methyl ethyl ketone and (methyl) or (ethyl) or (butyl) tetrahydrofurfuryl ether. Said absorption type refrigerator systems, however, are quite different in mechanism from the compression type refrigerator systems described above, and tetraethylene glycol dimethyl ether described in the Examples of the above patent is not proper as a lubricating oil for compression type refrigerator systems if just because of its particularly low viscosity.

Thus, lubricating oils for compression type refrigerator systems having sufficiently good miscibility with R-134a and high lubricating properties have not been found yet, and their development has been eagerly desired.

An essential requirement of the lubricating oil for refrigerator systems is a wide temperature range for compatibility with the refrigerant (compatibility) which means no clouding at high temperature (high salvation of the refrigerant to the lubricating oil), high molecular polarity of the lubricating oil and no separation of the lubricating oil from the refrigerant at low temperature (high solubility of the lubricating oil to the refrigerant, and low molecular weight of lubricating base oil). For this reason, high compatibility with the refrigerant is very important, and it is necessary that the substance is not separated from the refrigerant at high or low temperatures and that it does not react with it. If the compatibility with the refrigerant is low, the equipment may seize on the portion of the refrigerator system which is subject to high temperature.

The man in the art knows how to determine and how to obtain the suitable viscosity of a lubricating oil in function of the type of refrigerator system used.

Further, the lubricating oil for a refrigerator system should not be corrosive to the refrigerating equipment, should preferably not reduce its insulating properties, and has to have high stability to the refrigerant.

Also, the lubricating oil for a refrigerator system should improve the wear-resistant properties of aluminum components in piston and bearings, made of iron and aluminum, of the refrigerator system.

An object of the present invention is to provide a lubricating oil for a refrigerator system suitable for the use in the refrigerator system using refrigerants such as hydrofluorocarbons including 1,1,1,2-tetrafluoroethane, having a wide compatibility temperature range with the refrigerant.

Another object of the present invention is to provide a lubricating oil having no corrosive properties to refrigerating equipment.

Yet another object of the present invention is to provide a lubricating oil showing little or no reduction in insulating properties.

A further object of the present invention is to provide a lubricating oil having a high stability to the refrigerant.

Yet a further object of the present invention is to provide a lubricating oil improving the wear-resistant properties of equipment components.

Still a further object of the present invention is to provide a lubricating oil suitable for use in compression type refrigerator systems using hydrofluorocarbons and particularly R134 or R134a.

SUMMARY OF THE INVENTION

According to the present invention, there is provided a refrigeration compressor lubrication additive or lubricating oil, compound (X), that can be prepared by esterification of a polyoxyethylene represented by the following formula (I):

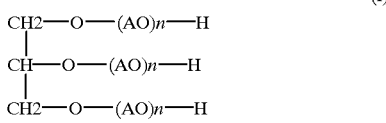

(I)

wherein each n, which may be different from the others, represents an integer from 1 to 10, preferably from 1 to 3, and AO is the oxyethylene group, with at least one polycarboxylic acid compound having from 2 to 20 carbon atoms, preferably from 4 to 13 carbon atoms, and at least one monocarboxylic acid compound having from 2 to 20 carbon atoms, preferably from 6 to 13 carbon atoms.

DESCRIPTION OF THE PREFERRED EMBODIMENTS

The polyoxyethylene components used in the present invention (formula (I)) can be obtained by reacting glycerol and ethylene oxide in the presence of a catalyst consisting of potassium hydroxide. Preparation methods of such polyoxyethylenes are given in the examples hereafter.

The polycarboxylic acid compound used in the present invention is preferably chosen among the dicarboxylic acid compounds.

The term dicarboxylic acid compound as used in the present invention also includes, in addition to usual dicarboxylic acids, chemical compounds directly derived from such acids such as anhydrides or acyls.

Preferably the polycarboxylic acid compounds used in the present invention are selected from adipic acid, trimellitic acid, succinic acid, succinic anhydride, phthalic acid, phthalic anhydride, or any other suitable derivatives thereof, succinic anhydride being the most preferred.

The monocarboxylic acid compounds which may be used in the present invention include monocarboxylic acids which can be selected from hexanoic, heptanoic, octanoic, nonanoic, decanoic, dodecanoic, isovaleric, neopentanoic, 2-ethylbutyric, 2-methylpentanoic, 2-methylhexanoic, 2-ethylhexanoic, isooctanoic, isononanoic, isodecanoic, 2,2'-dimethyloctanoic and 2-butyloctanoic acids, and other suitable derivatives thereof, or mixtures thereof.

According to the present invention, the weight ratio of polycarboxylic to monocarboxylic acid compound used for the esterification of the polyoxyethylene (I) is preferably comprised between 0.1% and 20%, more preferably between 1% and 10%.

The compound (X) of the present invention can be obtained by reacting the obtained polyoxyethylene with the carboxylic acid compounds in the presence of a catalyst such as a tin oxalate. This reaction is usually performed at a temperature comprised between 130° C. and 260° C. and at a pressure comprised between sub-atmospheric and 5 bars, preferably below 2 bars.

According to another object of the present invention there is provided a compression type refrigerator system which comprises a hydrofluorocarbon as refrigerant and a lubricating oil characterized in that the lubricating oil contains the above-identified compound (X).

According to a further object of the present invention, the above-identified compound (X) is advantageously used in the closed system of a refrigerator system using hydrofluorocarbon as refrigerant.

Preferably, the hydrofluorocarbon is a R-134a (1,1,1,2-tetrafluoroethane) or a R-134 (1,1,2,2-tetrafluoroethane) refrigerant.

According to a preferred embodiment of the present invention, the refrigerator system is of the compression type.

According to a further embodiment of the present invention, the compound (X) is used as lubricating oil or as additive in a lubricating oil.

When the compound (X) is used as additive in a lubricating oil there is preferably used as base oil a compound (M) which can be represented by the following formula (II):

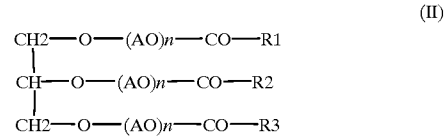

(II)

wherein AO is the oxyethylene group, each n (which may be different from the others) is an integer from 1 to 10, preferably from 1 to 3, and R1, R2, R3, which can be the same or different, are linear or branched alkyl groups having from 1 to 19 carbon atoms, preferably from 5 to 12 carbon atoms.

According to the present invention, the lubricating oil used contains at least 1% by weight of the compound (X), preferably at least 5% by weight.

The Applicant has found that by using the compound (X) of the present invention, the resulting lubricating oil for compression type refrigerator systems containing such compounds had low hygroscopic properties.

Further, a high thermal stability and high lubricating properties were obtained by using the compound (X) of the present invention.

Still further the required properties of miscibility with hydrofluorocarbons were obtained with the lubricating oils of the present invention.

While not wanting to be bound by a theory, the Applicant believes that these excellent properties were obtained thanks to the use of polycarboxylic acid compounds during the esterification of the polyoxyethylene; indeed, the presence of polycarboxylic acid compounds leads to the bridging of different polyoxyethylene compounds which gives lubricating oils with improved properties.

The present invention will now be illustrated by some examples which are not limitative.

EXAMPLES

1. Ethoxylation of 1,2,3-propanetriol a) Glycerol 3EO

In a 600 cm3 pressure reactor fitted with heating, mixing and cooling means and temperature control was charged 179.5 g (1.951 mole) of glycerol and 0.18 g of potassium hydroxide. The reactor was flushed with nitrogen and heated to 140° C. under nitrogen pressure (2.104 Pa) with mixing. At this temperature 257.6 g (5.854 mole) of ethylene oxide was added within 1 hour after which temperature and mixing were maintained a further 30 minutes to complete the reaction. The reactor was then cooled and the product (435.8 g) recovered as a pale yellow liquid.

Glycerol content and hydroxyl value were determined on the product (% free glycerol by titration with periodic acid, hydroxyl value by reaction with acetic anhydride).

% free glycerol:5.7 hydroxyl value:723.1 b) Glycerol 6EO

Example a) hereabove is repeated with different amounts of reactants:

| | |
|---|---|
| 109.2 g glycerol | (1.187 mole) |
| 313.5 g ethylene oxide | (7.125 mole) |
| 0.19 g KOH | |
| 422.7 g product recovered | (0.31% free glycerol, 459.3 hydroxyl value) | c) Glycerol 9E0

Example a) hereabove is repeated with different amounts of reactants:

| | |
|---|---|
| 85.1 g glycerol | (0.925 mole) |
| 366.4 g ethylene oxide | (8.327 mole) |
| 0.17 g KOH | |
| 449.1 g product recovered | (0.04% free glycerol, 329.1 hydroxyl value) |

2. Lubricating oil preparation a) Compound (X)

To a reactor fitted with heating/cooling and mixing means and temperature control, was charged 1000 g of glycerol 9EO (example 1c) hereabove) and 70 g of succinic anhydride. The reactor was heated to 135° C. and 3.7 g of tin oxalate at about 80° C. were then added to the reactor. After 1 hour 30', 812 g of "CEKANOIC" acid (trademark of EXXON; C8/C9/C10 acid) were added while heating quickly up to 180° C. under nitrogen. Then over a period of one hour, the temperature was increased up to 230° C. Water was removed by distillation and the reactor was cooled down to 100° C. Then the excess of acid was removed by distillation under a pressure of 20 mbars.

The reactor was then cooled to 40° C. and the esterified polyethoxylated glycerol 9EO recovered (compound X1).

The properties of this compound A are given in table 1 hereafter (grade a).

b) Compound (M)

To a reactor fitted with heating/cooling and mixing means and temperature control, was charged 620 g of glycerol 3EO (example 1a) hereabove) and 1235.1 g of heptanoic acid. The reactor was heated to 170° C. under nitrogen with mixing. 3.7 g of tin oxalate at about 80° C. were then added to the reactor.

Then within four hours, the reactor is progressively heated up to 230° C. Then water and the excess of acid were respectively removed by distillation under a relative vacuum from 200 to 20 mbars.

The reactor was then cooled to 40° C. and the esterified polyethoxylated glycerol 3EO recovered (compound M1).

c) Several lubricating oils were prepared by mixing at ambient temperature the above compounds X1 and M1 with the respective weight percentages indicated hereunder. The viscosity at 40° C. and the viscosity index of these lubricating oils were measured according to ASTM-D-445. The falex test was measured according to ASTM-D-2670.

TABLE 1

| | Grade: | | | | | |
|---|---|---|---|---|---|---|
| | a | b | c | d | e | f |
| Compound X1 | 100 | 80 | 60 | 45 | 15 | 5 |
| Compound M1 | 0 | 20 | 40 | 55 | 85 | 95 |
| Viscosity (cSt) | 100 | 68 | 46 | 32 | 22 | 17 |
| Viscosity index | 164 | 172 | 181 | 176 | 170 | — |
| Falex test (teeth) | — | — | 32 | — | 25 | — |

(—) means not measured

Further, all the above grades were tested for compatibility with R-134A refrigerant. The results showed that they were all perfectly miscible in all proportions with the refrigerant until −50° C.

What is claimed is:

1. A compound suitable for use as a compressor lubricant, comprising an oil prepared by esterification of a polyoxyethylene represented by the following formula (I):

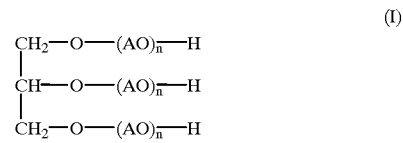

wherein each n, which may be different from the others, represents an integer from 1 to 10, and AO is the oxyethylene group, with at least one polycarboxylic acid compound having from 2 to 20 carbon atoms, and at least one monocarboxylic acid compound having from 2 to 20 carbon atoms.

2. The compound according to claim 1 wherein the polycarboxylic acid compound is a dicarboxylic acid compound.

3. The compound according to claim 2 wherein the dicarboxylic acid compound is succinic anhydride.

4. The compound according to any of the preceding claims wherein the weight ratio of polycarboxylic to monocarboxylic acid compound used for the esterification of the polyoxyethylene (I) is comprised between 0.1% and 20%.

5. The compound according to claim 4 wherein the compound is mixed with a hydrofluorocarbon selected from the group consisting of R-134a (1,1,1,2-tetrafluoroethane) and R-134 (1,1,2,2-tetrafluoroethane).

6. A compression refrigerator system comprising a hydrofluorocarbon as refrigerant and a lubricating oil characterised in that the lubricating oil contains the compound according to claim 1.

* * * * *